United States Patent
Moberg-Alehammar et al.

(10) Patent No.: US 7,763,770 B2
(45) Date of Patent: Jul. 27, 2010

(54) ABSORBENT ARTICLE WITH IMPROVED SURFACE MATERIAL

(75) Inventors: Barbro Moberg-Alehammar, Mölndal (SE); Anna Nihlstrand, Mölndal (SE); Anna-Karin Storm, Göteborg (SE); Anna Bagger-Sjöbäck, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 808 days.

(21) Appl. No.: 10/788,446

(22) Filed: Mar. 1, 2004

(65) Prior Publication Data

US 2004/0181199 A1  Sep. 16, 2004

Related U.S. Application Data

(60) Provisional application No. 60/454,343, filed on Mar. 14, 2003.

(51) Int. Cl.
  *A61F 13/15*   (2006.01)
  *A61F 13/20*   (2006.01)
(52) U.S. Cl. .................... 604/378; 604/385.01
(58) Field of Classification Search ................. 604/367, 604/378, 385, 385.01
  See application file for complete search history.

(56) References Cited

U.S. PATENT DOCUMENTS 5,509,915 A * 4/1996 Hanson et al. ............... 604/378
5,728,081 A * 3/1998 Baer et al. ................... 604/370
5,968,855 A   10/1999 Perdelwitz, Jr.

FOREIGN PATENT DOCUMENTS

| CA | 2060744 | 3/1993 |
|---|---|---|
| EP | 0312118 A2 | 4/1989 |
| GB | 2339477 A | 1/2000 |
| JP | H05-261126 | 10/1993 |
| JP | 2002-540848 | 12/2002 |
| WO | 98/51250 A1 | 11/1998 |
| WO | WO 00/59431 | 10/2000 |

OTHER PUBLICATIONS

Meilgaard, M. et al., Sensory Evaluation Techniques, $2^{nd}$ Edition, pp. 117-119, CRC Press Inc., Boca Raton (1991).
Miller, B. et al., "Liquid Porosimetry: New Methodology and Applications", Journal of Colloid and Interface Science 162, pp. 163-170, Academic Press (1994).
*Notice of Reasons for Rejection*, Corresponding Japanese Application No. 2006-507957, mailed Oct. 13, 2009.

* cited by examiner

*Primary Examiner*—Michele Kidwell
(74) *Attorney, Agent, or Firm*—Buchanan Ingersoll & Rooney PC

(57) ABSTRACT

An absorbent article comprises an absorbent body, a liquid-permeable covering layer arranged over a first surface on the absorbent body, and a liquid-permeable liquid-transfer layer arranged between the absorbent body and the liquid-permeable covering layer. The liquid-permeable covering layer comprises a nonwoven material with a pore volume distribution curve with a maximum at a pore radius greater than or equal to 50 μm and with a wetting angle of at least 120°. The liquid-transfer layer comprises a fibrous layer with a pore volume distribution curve with a maximum at a pore radius of from 105 to 325 μm.

21 Claims, 5 Drawing Sheets

Increased degree of dryness →

N3V2　　N3V10　　N6V3　　N7V10　　N8V6　　N9V6
　　N2V9　　　　　　N9V8　　N5V4　　　N1V6
　　　　N1V2　　　　　　　N4V1

Groups: A　B　B　BC　C　C　D　DD　E　E　F

FIG.6

ABSORBENT ARTICLE WITH IMPROVED SURFACE MATERIAL

CROSS-REFERENCE TO RELATED APPLICATIONS

This application claims the benefit of U.S. Provisional Application No. 60/454,343, entitled "Absorbent Article with Improved Surface Material," filed on Mar. 14, 2003, the entire contents of which are hereby incorporated by reference.

BACKGROUND OF THE INVENTION

1. Technical Field

Embodiments of the invention relate absorbent articles comprising an absorbent body, a liquid-permeable covering layer arranged over a first surface on the absorbent body, and a liquid-permeable liquid-transfer layer arranged between the absorbent body and the liquid-permeable covering layer.

2. Background Art

Disposable absorbent articles, such as diapers, incontinence pads, bed protectors, sanitary towels, etc., which are intended to receive and absorb bodily discharges such as urine, menstrual blood and motions have been well known for a long time. Absorbent articles of this kind usually comprise a liquid-permeable covering layer and a liquid-impermeable covering layer, with an absorbent body enclosed between the covering layers. Especially in the case of urine absorption, it is essential in this connection that the absorbent article and, in particular, the liquid-permeable covering layer is capable of receiving and rapidly admitting liquid. It is also important for the surface of the article to be kept as dry as possible even after wetting and for liquid which has passed into the article to remain there and not leak back out towards the body of the user. This phenomenon is usually referred to as rewetting and is highly undesirable.

The requirements for rapid admission of liquid into an absorbent article and also a dry surface and low rewetting are in part incompatible. A close liquid-permeable covering material with fine pores therefore affords good protection against rewetting but leads to the liquid-admission capacity being low. This often results in liquid not being taken up by the absorbent article but instead running out on the surface of the article and causing leakage. Moreover, a fine-pored material tends to retain liquid after wetting, which makes the surface of the article feel wet. A coarse-pored surface material has a good capacity for rapidly admitting liquid and does not to any great extent retain liquid in the pores. On the other hand, such a material offers poor protection against rewetting. A loose material moreover has a low masking effect, which means that colored bodily fluid such as menstrual blood is clearly visible through the covering material.

In order to remedy the abovementioned problems, it has been proposed to combine different types of liquid-permeable material. EP 0 312 118, for example, describes an absorbent article with a liquid-permeable covering layer arranged over the absorbent body of the article and with a likewise liquid-permeable transport layer arranged between the surface layer and the absorbent body. The transport layer has lower hydrophilicity than the absorbent body and moreover has an effective average pore size which is smaller than the pore size in the surface layer.

U.S. Pat. No. 5,968,855 describes a nonwoven material which is stated to have good liquid-transport properties and can be used as a transport layer in an absorbent article.

In spite of great efforts having been made in order to improve the liquid-permeable covering layer on an absorbent article, it has hitherto not been possible for an optimum combination of covering material and liquid-transfer material to be presented. A main object of the invention is therefore to offer an improved surface material combination, which makes possible both rapid liquid admission and a dry surface with low rewetting.

OBJECTS AND SUMMARY

In accordance with embodiments of the invention, an absorbent article of has therefore been produced, which article comprises a liquid-permeable covering layer including a nonwoven material with a pore volume distribution curve with a maximum at a pore radius greater than or equal to 50 μm and with a wetting angle of at least 120°, and the liquid-transfer layer includes a fibrous layer with a pore volume distribution curve with a maximum at a pore radius of from 105 to 325 μm.

Advantageously, in one embodiment, the liquid-permeable covering layer has a pore volume distribution curve with a maximum at a pore radius greater than or equal to 55 μm and preferably with a maximum at a pore radius of from 55 μm to 60 μm.

Furthermore, in one embodiment, the liquid-permeable covering layer can include fibers with a fiber fineness of at least 5 dtex.

In one embodiment, the liquid-permeable covering layer suitably has a basis weight of at most 15 $g/m^2$.

In a preferred embodiment, an especially advantageous material for use as a liquid-permeable covering layer has been found to be a relatively hydrophobic spunbond material. Such a material does not spread liquid in the layer, which carded nonwoven materials have a tendency to do.

Furthermore, in another embodiment, it is advantageous if the liquid-transfer layer has a pore volume distribution curve with a maximum at a pore radius of from 115 μm to 185 μm and preferably with a maximum at a pore radius of from 135 μm to 155 μm.

In one embodiment, it is furthermore suitable if the liquid-transfer layer has a cumulative pore volume in the pore size range 110 to 350 μm which is more than 60% of the total pore volume and preferably more than 65% of the total pore volume. In this connection, it is preferred if the liquid-transfer layer has a cumulative pore volume in the pore size range 120 to 230 μm which is more than 40% of the total pore volume and preferably more than 50% of the total pore volume, and it is most preferable if the liquid-transfer layer has a cumulative pore volume in the pore size range 150 to 180 μm which is more than 15% of the total pore volume and preferably more than 20% of the total pore volume.

In one embodiment, the liquid-transfer layer suitably consists of fibers with a fiber fineness of from 6.7 to 11 dtex.

Furthermore, in one embodiment, the liquid-transfer layer advantageously has a basis weight of from 10 gsm to 100 gsm, preferably from 25 gsm to 60 gsm, and a bulk of at least 15 $cm^3/g$ measured at a load of 0.1 kPa.

It has also been found to be advantageous in an embodiment if the liquid-transfer layer has a pore volume distribution curve with a maximum located at from 135 μm to 155 μm in combination with a cumulative liquid volume of 0.1 mm3/mg of sample and preferably 0.5 mm3/mg or more in pores with radii smaller than or equal to 25 μm.

The absorbent article according to embodiments of the invention is, for example, a diaper, an incontinence pad, a sanitary towel, a bed protector or the like and suitably comprises a liquid-impermeable covering layer located over a second surface on the absorbent body opposite the first surface, where the liquid-permeable covering layer and the liquid-impermeable covering layer together enclose the absorbent body.

With regard to both surface dryness and liquid take-up time, it is important, as mentioned above, to use open materials with relatively large pores. It was not previously known, however, which degree of openness gives the best combination of liquid admission and surface dryness.

By virtue of the embodiments of the invention, it is possible to produce absorbent articles with extremely good liquid-handling properties. With knowledge of the nature of a certain material combination, it is also possible to predict how the material combination will behave when it is used on an absorbent article.

As far as dryness is concerned, the properties of both the liquid-permeable covering layer and the liquid-transfer layer are important, although the properties of the liquid-transfer layer have the greatest influence on the dryness. In this connection, the pore volume distribution (PVD), in particular, is significant.

BRIEF DESCRIPTION OF FIGURES

The invention will be described below with reference to the figures shown in the accompanying drawings.

FIG. 6 shows results of sensory dryness measurements.

DETAILED DESCRIPTION OF THE PREFERRED EMBODIMENTS

Figure 1:
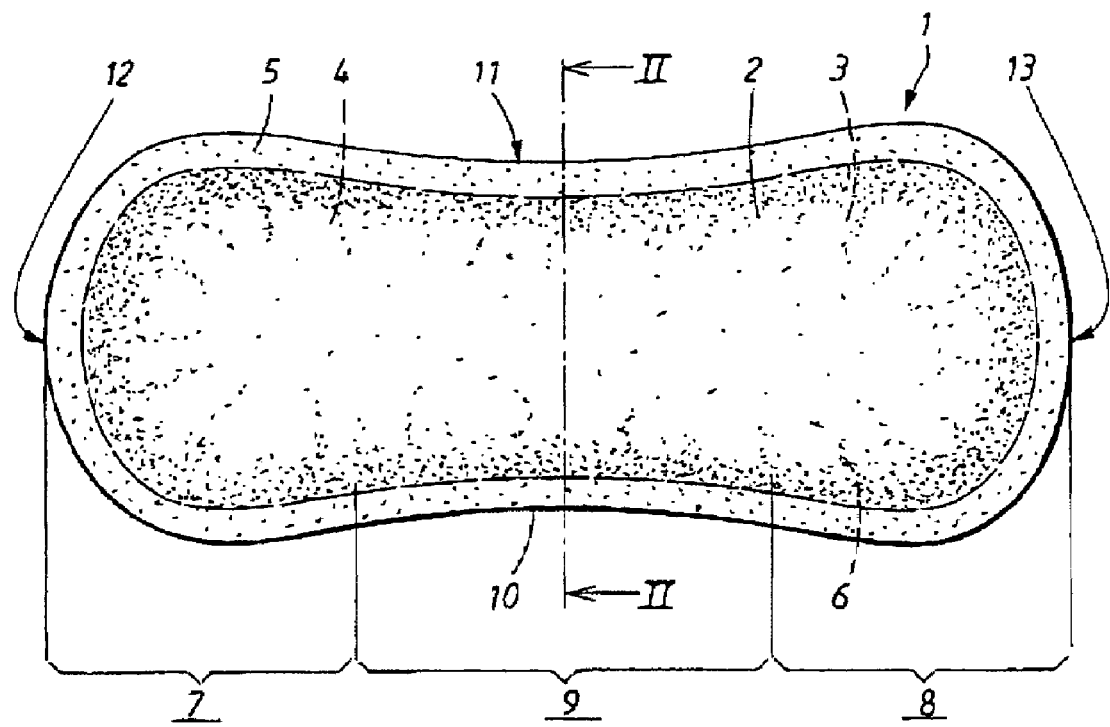
FIG. 1 shows an incontinence pad with a surface material according to an embodiment of the invention.
Figure 2:
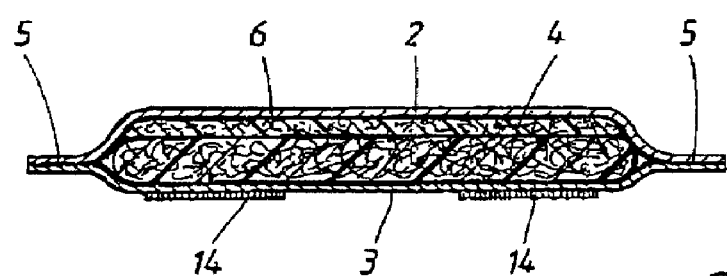
FIG. 2 shows a section along the line II-II through the diaper in FIG. 1.

The incontinence pad 1 shown in FIGS. 1 and 2 comprises a first, liquid-permeable covering layer 2, a second, liquid-impermeable covering layer 3, and an absorbent body 4 enclosed between the covering layers. The two covering layers 2, 3 have a slightly greater extent in the plane than the absorbent body 4 and project beyond the absorbent body 4 around its entire periphery. The covering layers 2, 3 are interconnected within the projecting portions 5, for example by means of gluing or welding using heat or ultrasound.

In accordance with the invention, the liquid-permeable covering layer 2 consists of a layer of nonwoven material. Especially preferred nonwoven materials are spunbond materials.

The liquid-impermeable covering layer 3 can consist of a liquid-impermeable plastic film, a nonwoven layer which has been coated with a liquid-blocking material, or another flexible material layer which is capable of resisting liquid penetration. In general, it is an advantage if the liquid-impermeable covering layer 3 has a certain breathability, i.e., allows the passage of water vapor through the layer 3.

Furthermore, a liquid-permeable liquid-transfer layer 6 is arranged between the liquid-permeable covering layer 3 and the absorbent body 4. Such a liquid-transfer layer 6 consists of a bulky fibrous material with large internal volume. Suitable materials for the liquid-transfer layer 6 are various types of preferably bonded fiber waddings, for example, carded, adhesive-bonded or thermally bonded wadding.

The incontinence pad 1 has an elongate shape, with wider end portions 7, 8 and a narrower crotch portion 9. The crotch portion 9 is the part of the incontinence pad 1 which is intended to be arranged in the crotch of the wearer during use and serve as the receiving surface for the bodily fluid which is discharged into the incontinence pad 1. The incontinence pad 1 also has two inwardly curved, longitudinal side edges 10, 11 and two end edges 12, 13.

Arranged on the outside of the liquid-impermeable covering layer 3 is a fastening means 14 in the form of two transverse areas of self-adhesive glue. Before use, the fastening means 14 is suitably covered by a removable protective layer (not shown in the drawing) of release-agent-treated paper, plastic film, or the like. Instead of the glue pattern in the form of two transverse glue areas shown, a number of other glue patterns can be used, such as one or more longitudinal areas, dots, full coating etc. Alternatively, other types of fastening means can be used, such as hook and loop surfaces, press studs, belts, special briefs or the like.

An incontinence pad 1 of the kind shown in the figures is primarily intended for use by people with relatively mild incontinence and is therefore of such a size that it can easily be accommodated inside a pair of ordinary briefs. In this connection, the fastening means 14 serves to hold the incontinence pad in place inside the briefs during use.

The absorbent body 4 is shown diagrammatically and includes absorbent material. The absorbent body 4 can comprise one or more layers which can be the same or different with regard to composition, shape, size, and positioning in the incontinence pad.

Absorption materials which can be used are cellulose fibers, the most common in this respect being cellulose fluff pulp, various types of absorbent foam material, and also what are known as superabsorbents, which are polymer materials which absorb liquid corresponding to many times their own weight while forming a liquid-containing gel. Superabsorbents are available in the form of fibers, particles, granules, film, etc. and can be mixed with other absorption materials or be arranged in separate layers or areas.

Although, for the purpose of illustration, the invention has been described here on the basis of an incontinence pad, it is of course the case that other types of absorbent article, such as diapers for children and adults, bed protectors, seat protectors, sanitary towels or the like are also covered by the invention. Absorbent articles such as, e.g., diapers can comprise further components which have not been described here. Examples of such components are elastic means, fastening-together means, wet indicators, raised portions, side barriers etc.

EXAMPLES

In order to determine the properties of different liquid-permeable covering materials and liquid-transfer layers, and to assess the suitability of different material combinations with regard to dryness and liquid-admission capacity, a number of measurements were performed.

Measuring Methods

Determination of wetting angle: DAT (Dynamic Absorption Tester)

Figure 3:
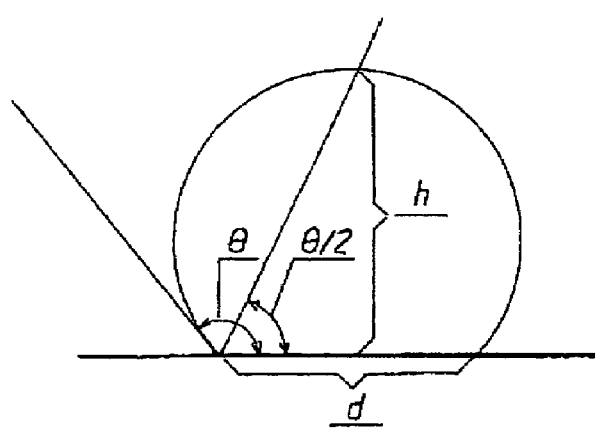
FIG. 3 shows a drop of liquid arranged on a surface.

In order to determine the degree of hydrophobicity of suitable liquid-permeable covering materials, the following method was used:

A drop of liquid is applied to a test material while a video system films the procedure. Depending on the nature of the test material, the drop may remain lying on top of the material or be absorbed. By measuring the base (d) and the height (h) as shown in FIG. 3, the contact angle θ formed between the liquid and the material can be calculated with the aid of the following equation:

$$\tan\frac{\theta}{2} = \frac{2 \cdot h}{d}$$

The contact angle θ is stated as a function of the time, t, which passed from the drop coming into contact with the surface of the test material. In the examples below, the contact angle is shown at t=0.1 s, when all the drops were still lying on the surface.

All the test materials were conditioned for at least 4 h before measurement (23° C.; 50% relative humidity). The measurements were carried out on a Fibro 1100 DAT system from Fibro System AB, Sweden, in accordance with the associated manual (software version: DAT WinNT 3.0). Water was used as the test liquid and the drop volume was 5 μl. 25 drops were measured for each material.

The materials for which the contact angle was determined were:

N1: A spunbond nonwoven with a weight per unit area of 17.9 g/m² and a fiber fineness of 3.2 dtex.
N2: A spunbond nonwoven with a weight per unit area of 14.9 g/m² and a fiber fineness of 3.8 dtex.
N3: A spunbond nonwoven with a weight per unit area of 15.9 g/m² and a fiber fineness of 3.7 dtex.
N4: A spunbond nonwoven with a weight per unit area of 11.3 g/m² and a fiber fineness of 4.9 dtex.
N7: A spunbond nonwoven with a weight per unit area of 13.3 g/m² and a fiber fineness of 5.4 dtex.
N9: A spunbond nonwoven with a weight per unit area of 13.2 g/m² and a fiber fineness of 7.1 dtex.
N10: A spunbond nonwoven with a weight per unit area of 22 g/m² and a fiber fineness of 2.3 dtex.
N11: A spunbond nonwoven with a weight per unit area of 16 g/m² and a fiber fineness of 3.6 dtex.

The result of the measurements is indicated in Table 1.

TABLE 1

Wetting angles

| Material | Contact angle (t = 0.1 s) | Number of drops measured |
|---|---|---|
| N1 | 125 | 25 |
| N2 | 124 | 25 |
| N3 | 116 | 25 |
| N4 | 123 | 25 |
| N5 | 123 | 25 |
| N6 | 121 | 25 |
| N7 | 114 | 25 |
| N8 | 120 | 25 |
| N9 | 123 | 25 |
| N10 | 0 | 25 |
| N11 | 122 | 25 |

Determination of Pore Volume Distribution

The pore volume distribution for different liquid-permeable covering materials and liquid-transfer materials was determined using the method described in Journal of Colloid and Interface Science 162:163-170 (1994). The method used is based on measurements of the quantity of liquid which can be pressed out of a porous material ("receding mode") at a certain pressure, and the result of the measurement is presented in the form of a curve in a chart where the curve illustrates the overall pore volume for a given pore radius.

Running Conditions for Liquid-Permeable Covering Layer (Nonwoven)

In the measurements, n-hexadecane (>99%, Sigma H-0255) was used as the measuring liquid. Measurement was carried out on circular samples with an area of 25.5 cm². The sample was placed in the chamber and was saturated with the test liquid. Millipore 0.22 μm cat. no. GSWP 09000 was used as the membrane. In order to achieve good contact between the sample and the membrane, a load covering the whole sample surface was placed on top of the sample. In order to avoid measuring pores between the sample surface and the weight, a large-pore polyurethane foam (which does not hold liquid) was moreover placed between the sample and the weight applied. The total load on the sample was 0.15 kPa. In order for it to be possible to record the remaining liquid, the sample was weighed before and immediately after running was completed.

The equilibrium speed, i.e., the speed when the weight change at the selected pore radius has decreased to an insignificant level, was set at 2 mg/min, and the measuring time during which the weight change was recorded was set at 30 seconds.

Measurements were carried out at pressures corresponding to the following pore radii [μm]:

| | | | | | |
|---|---|---|---|---|---|
| 500 | 400 | 300 | 250 | 225 | 200 |
| 175 | 150 | 125 | 110 | 100 | 90 |
| 80 | 70 | 60 | 55 | 50 | 45 |
| 40 | 35 | 40 | 25 | 20 | 15 |
| 10 | 8 | 6 | 4 | 2 | |

In addition to measurement on samples, what is known as a blank run was carried out. In a blank run, only foam and load are placed in the test chamber. Measurement is performed in the same way and with the same running conditions as when samples are measured. The blank run is then subtracted from the test run before further processing of raw data.

Running Conditions for Liquid-Transfer Layer (Wadding)

In the measurements, a 0.1% w/w solution of Triton TX-100 (Calbiochem—648462) was used as the measuring liquid. Measurement was carried out on circular samples with an area of 25.5 cm². The sample was placed in the chamber and was saturated with the test liquid. Millipore 0.22 μm cat. no. GSWP 09000 was used as the membrane. In order to achieve good contact between the sample and the membrane, a load covering the whole sample surface was placed on top of the sample. In order to avoid measuring pores between the sample surface and the weight, a large-pore polyurethane foam (which does not hold liquid) was moreover placed between the sample and the weight applied. The total load on the sample was 0.57 kPa.

The equilibrium speed, i.e., the speed when the weight change at the selected pore radius has decreased to an insignificant level, was set at 5 mg/min, and the measuring time during which the weight change was recorded was set at 30 seconds.

Measurements were carried out at pressures corresponding to the following pore radii [μm]:

| 700 | 600 | 500 | 400 | 350 | 300 |
|---|---|---|---|---|---|
| 275 | 250 | 240 | 230 | 220 | 210 |
| 200 | 190 | 180 | 170 | 160 | 150 |
| 140 | 130 | 120 | 110 | 100 | 90 |
| 80 | 70 | 60 | 50 | 40 | 30 |
| 25 | 20 | 15 | 10 | 5 | |

In addition to measurement on samples, a blank run was carried out. In a blank run, only foam and load are placed in the test chamber. Measurement is performed in the same way and with the same running conditions as when samples are measured. The blank run is then subtracted from the test run before further processing of raw data.

The wadding materials for which the pore volume distribution was determined were:

V1: An adhesive-bonded polyester wadding with a weight per unit area of 43.0 g/m$^2$ and a fiber fineness of 5.3 dtex.
V2: An adhesive-bonded polyester wadding with a weight per unit area of 34.1 g/m$^2$ and a fiber fineness of 6.7 dtex.
V3: An adhesive-bonded polyester wadding with a weight per unit area of 50.4 g/m$^2$ and a fiber fineness of 6.7 dtex.
V4: An adhesive-bonded polyester wadding with a weight per unit area of 28.3 g/m$^2$ and a fiber fineness of 7.7 dtex.
V5: An adhesive-bonded polyester wadding with a weight per unit area of 38.0 g/m$^2$ and a fiber fineness of 7.7 dtex.
V6: An adhesive-bonded polyester wadding with a weight per unit area of 59.9 g/m$^2$ and a fiber fineness of 7.7 dtex.
V8: An adhesive-bonded polyester wadding with a weight per unit area of 50.7 g/m$^2$ and a fiber fineness of 8.8 dtex.
V9: An adhesive-bonded polyester wadding with a weight per unit area of 61.7 g/m$^2$ and a fiber fineness of 8.8 dtex.
V10: An adhesive-bonded polyester wadding with a weight per unit area of 50.0 g/m$^2$ and a fiber fineness of 6.7 dtex.

Figure 4:
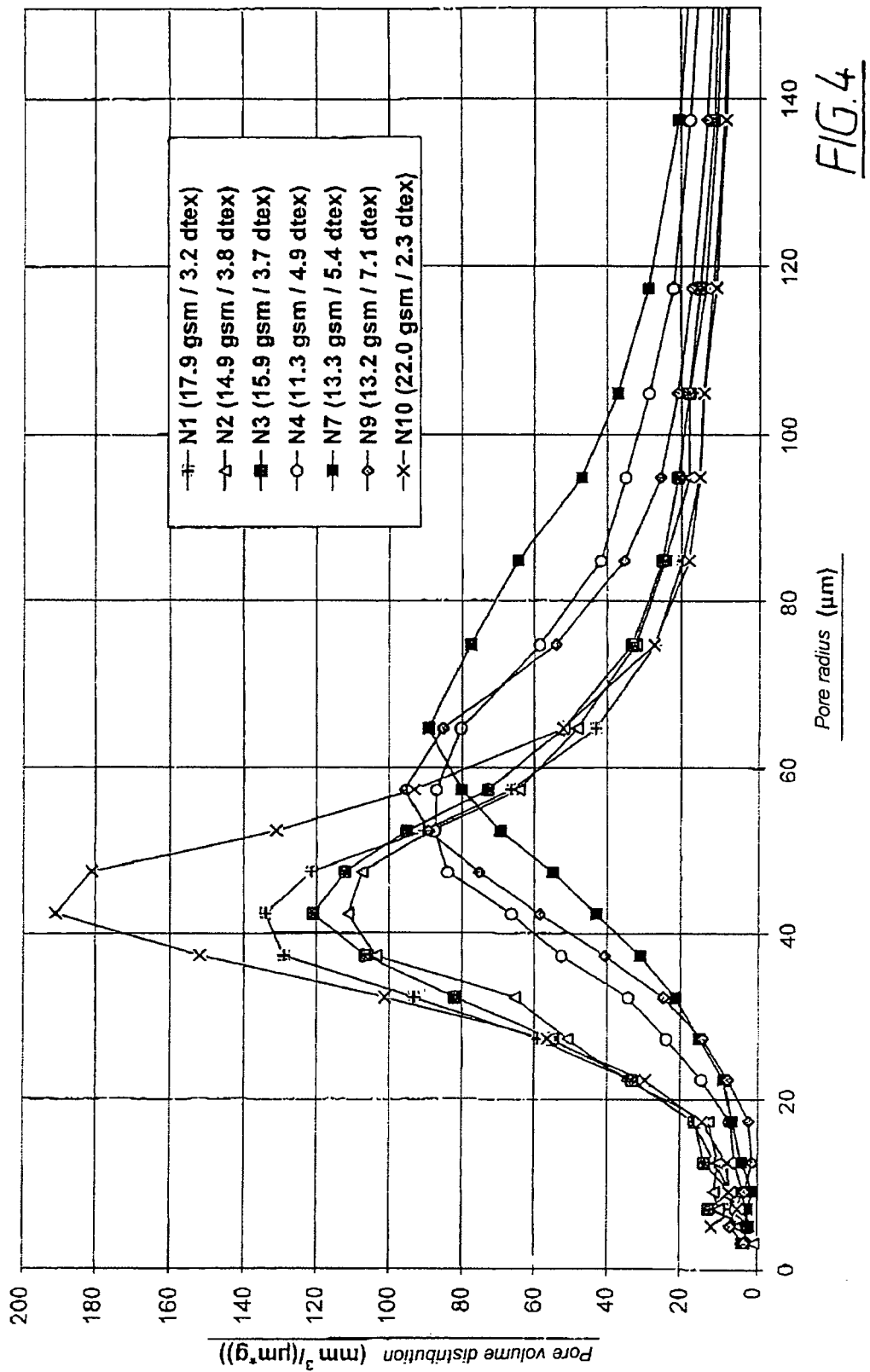
FIG. 4 shows a curve chart showing the pore volume distribution for liquid-permeable covering materials.
Figure 5:
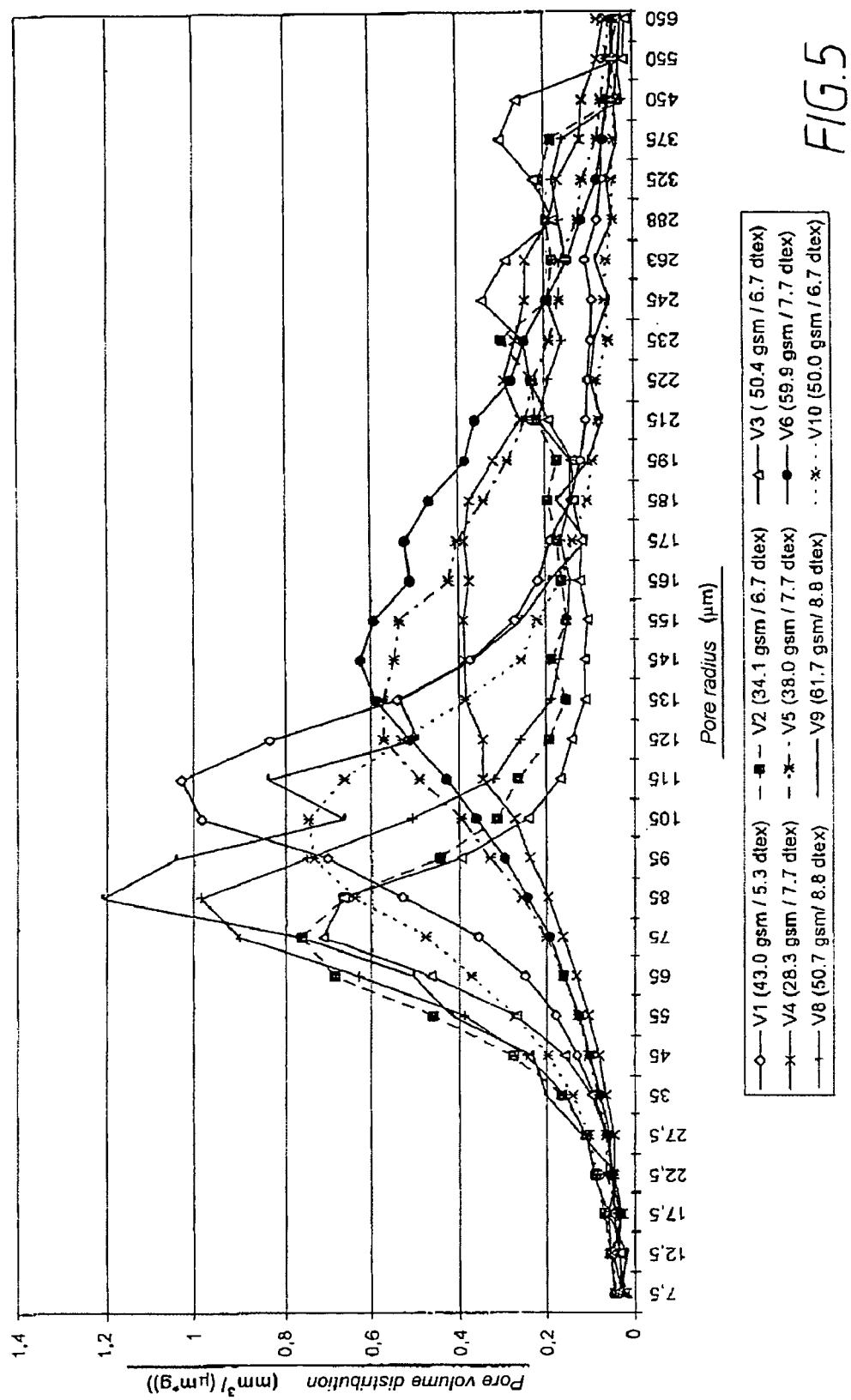
FIG. 5 shows a curve chart showing the pore volume distribution for liquid-transfer materials.

The results of the measurements are illustrated in the form of pore volume distribution curves in FIGS. 4 and 5.

FIG. 4 shows the pore volume distribution for different liquid-permeable covering materials. The samples on which measurements were performed were N1-N4, N7 and N9-N10, which were described above in connection with determination of hydrophobicity/contact angle.

The best pore volume distribution is that demonstrated by N9, but N4 is also very good, and the other tested materials show an acceptable pore volume distribution.

FIG. 5 illustrates the results of the measurements on different liquid-transfer materials, V1-V9, and a reference, V10.

Table 2 below shows the liquid percentage within the pore radius ranges 110-350 μm, 120-230 μm and 150-180 μm of the total cumulative volume in the range 0-700 μm for the samples V1-V10:

TABLE 2

Liquid percentage for different pore radius ranges

| | Pore radius range: | | |
|---|---|---|---|
| | 110-350 μm | 120-230 μm | 150-180 μm |
| V1 | 57.9 | 39.3 | 10.4 |
| V2 | 49.1 | 23.2 | 6.6 |
| V3 | 51.6 | 17.9 | 4.4 |
| V4 | 64.4 | 41.5 | 15.5 |
| V5 | 64.0 | 47.2 | 18.6 |
| V6 | 66.5 | 52.1 | 21.3 |
| V8 | 46.3 | 21.7 | 6.0 |
| V9 | 43.3 | 31.7 | 8.8 |
| V10 | 39.8 | 27.0 | 7.0 |

TABLE 2-continued

The liquid percentage within the ranges concerned provides a measure of how well defined a curve peak located within the range is.

Dryness Determination

The perceived dryness of the different material combinations was determined by sensory evaluation.

The test liquid was synthetic urine, SUM, made up as follows: 0.66 g/l magnesium sulphate, 4.47 g/l potassium chloride, 7.60 g/l sodium chloride, 18.00 g/l urea, 3.54 g/l potassium dihydrogen phosphate, 0.745 g/l sodium hydrogen phosphate, 1.00 g/l 0.1% triton, 0.4 g/l Nykockin (color) and the rest de-ionized water. The test liquid was applied to the samples in 3 doses of 100 ml, with intervals of 20 minutes between doses. The dryness evaluation was carried out 20 minutes after the last dose was added.

Different sensory methods were used in order to characterize the degree of dryness of the samples concerned:

Method 1: A panel consisting of people well informed of product type, evaluation procedure, and attribute were asked to place in order up to 10 samples on each occasion. All the samples are evaluated in a number of different combinations with other samples. The samples are evaluated blind. The ordering results are put together, and the samples are grouped so that each group consists of samples with similar dryness. For detailed information about the test procedure, see pages 117-199 of Sensory Evaluation Techniques, 2nd edition, ISBN 0-8493-4280-5. Authors: Meilgaard, Cicille & Carr.

Method 2: The samples within one and the same group are arranged in random order and evaluated by two expert evaluators. The expert evaluators are well informed of product type, evaluation procedure and attribute asked for. Samples within the same group are placed in order according to increasing degree of dryness. New groups are then formed from two similar groups in such a way that the driest samples from a wetter group and the wetter samples from a drier group are brought together, presented in random order and placed in order according to increasing degree of dryness. When all the original and newly formed groups have been placed in order in increasing degree of dryness, all the samples included are evaluated in the order produced. In the tests reported below, the samples were evaluated blind on all occasions.

As the samples consist of mutually different materials and material combinations, where the materials in themselves vary slightly, depending on where the sample is taken from, all evaluations were carried out several times.

Figure 7:
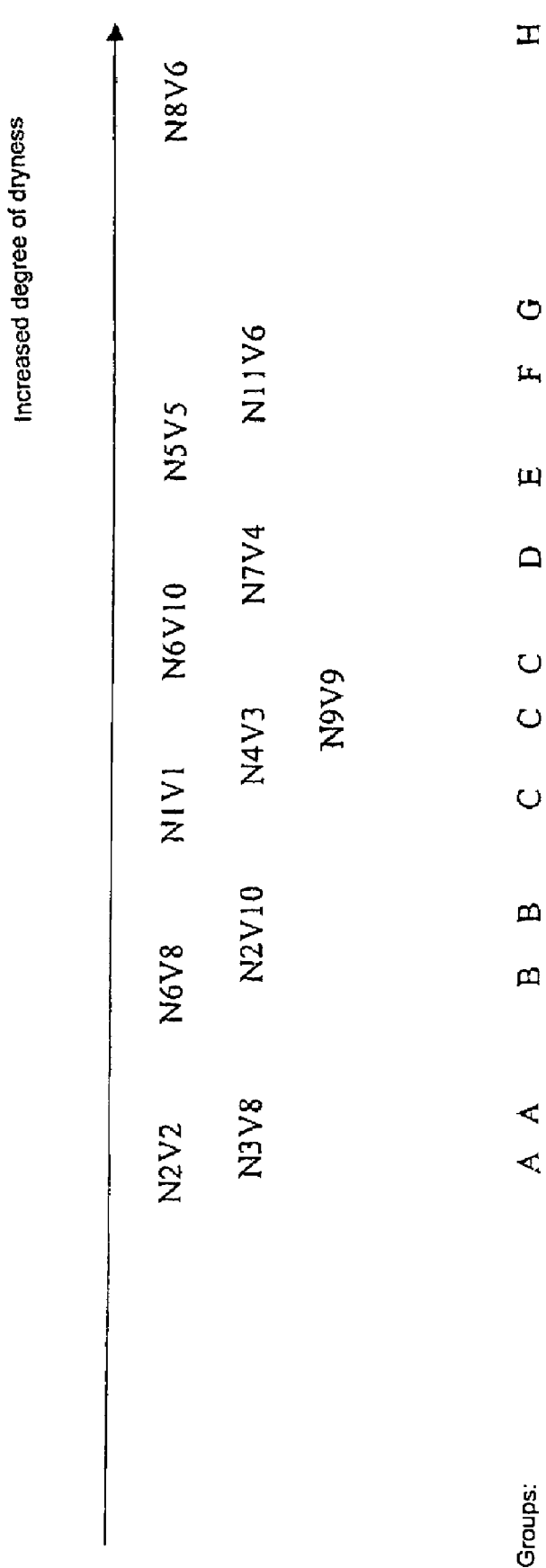
FIG. 7 shows results of sensory dryness measurements.

Results of dryness evaluations, performed according to method 2 above, for different combinations of surface material (NX) and underlying wadding (VX) are shown in FIGS. 6 and 7.

Liquid-Admission Speed

The capacity for rapidly taking up liquid and allowing it to pass through was measured for different material combinations. The measurements were carried out in accordance with the ART method which is described in detail in British patent specification GB 2 339 477.

The ART method is based on measuring the time it takes for an absorbent structure to receive a given quantity of liquid from a vessel, the quantity of liquid being measured continuously by measuring the quantity of liquid which is carried away from the vessel.

The results for the different material combinations tested are presented below in Table 3, which shows a comparison on a percentage basis of the admission times which were required to carry away the added quantity of liquid (SUM, made up as above) for different combinations of surface material and liquid-transfer layer, where the admission time for Sample 5 is set at 100 for doses 1, 2 and 3. The test liquid was added at 100 ml/dose with an 8 ml liquid column and at a pressure of 4.5 kg.

TABLE 3

| | Liquid-admission time | | | | | |
|---|---|---|---|---|---|---|
| ART | N9 + V6 Sample 1 | N9 + V2 Sample 2 | N3 + V6 Sample 3 | N3 + V4 Sample 4 | N10 + V10 Sample 5 | N9 + V1 Sample 6 |
| 1st dose | 96 | 112 | 92 | 197 | 100 | 84 |
| 2nd dose | 100 | 123 | 99 | 121 | 100 | 80 |
| 3rd dose | 96 | 123 | 109 | 126 | 100 | 93 |

Embodiments of the invention comprise all types of absorbent article intended for absorption of bodily fluids such as urine, loose motions and blood.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An absorbent article comprising:
an absorbent body,
a liquid-permeable covering layer arranged over a first surface of the absorbent body, and
a liquid-permeable liquid-transfer layer arranged between the absorbent body and the liquid-permeable covering layer, said liquid-permeable liquid-transfer layer being immediately adjacent said first surface of the absorbent body,
wherein the liquid-permeable covering layer comprises a nonwoven material with a pore volume distribution curve with a maximum at a pore radius greater than or equal to 50 μm and with a wetting angle of at least 120°, and
wherein the liquid-transfer layer comprises a fibrous layer with a pore volume distribution curve with a maximum at a pore radius of from 105 to 325 μm.

2. The absorbent article according to claim 1, wherein the liquid-permeable covering layer has a pore volume distribution curve with a maximum at a pore radius greater than or equal to 55 μm.

3. The absorbent article according to claim 2, wherein the liquid-permeable covering layer has a pore volume distribution curve with a maximum at a pore radius of from 55 μm to 60 μm.

4. The absorbent article according to claim 1, wherein the liquid-permeable covering layer comprises fibers with a fiber fineness of at least 5 dtex.

5. The absorbent article according to claim 1, wherein the liquid-permeable covering layer has a basis weight of at most 15 g/m².

6. The absorbent article according to claim 1, wherein the liquid-permeable covering layer comprises a spunbond nonwoven.

7. The absorbent article according to claim 1, wherein the liquid-transfer layer comprises a polyester wadding bonded with a binding agent.

8. The absorbent article according to claim 1, wherein the liquid-transfer layer has a pore volume distribution curve with a maximum at a pore radius of from 115 μm to 185 μm.

9. The absorbent article according to claim 8, wherein the liquid-transfer layer has a pore volume distribution curve with a maximum at a pore radius of from 135 μm to 155 μm.

10. The absorbent article according to claim 1, wherein the liquid-transfer layer has a cumulative pore volume in the pore size range of from 110 to 350 μm which is more than 60% of the total pore volume.

11. The absorbent article according to claim 10, wherein the liquid-transfer layer has a cumulative pore volume in the pore size range of from 120 to 230 μm which is more than 40% of the total pore volume.

12. The absorbent article according to claim 11, wherein the liquid-transfer layer has a cumulative pore volume in the pore size range of from 150 to 180 μm which is more than 15% of the total pore volume.

13. The absorbent article according to claim 1, wherein the liquid-transfer layer comprises fibers with a fiber fineness of from 6.7 to 11 dtex.

14. The absorbent article according to claim 1, wherein the liquid-transfer layer has a basis weight of from 10 gsm to 100 gsm, and a bulk of at least 15 cm³/g measured at a load of 0.1 kPa.

15. The absorbent article according to claim 1, wherein the liquid-transfer layer has a pore volume distribution curve with a maximum located at from 155 μm to 165 μm in combination with a cumulative liquid volume of 0.1 mm³/mg of sample or more in pores with radii smaller than or equal to 25 μm.

16. The absorbent article according to claim 1, wherein the article comprises a liquid-impermeable covering layer located over a second surface on the absorbent body opposite the first surface, and in that the liquid-permeable covering layer and the liquid-impermeable covering layer together enclose the absorbent body.

17. The absorbent article according to claim 1, wherein the first surface on the absorbent body defines a user-facing surface.

18. The absorbent article according to claim 1, wherein the absorbent body comprises one or more layers of material.

19. The absorbent article according to claim 1, wherein said liquid-permeable liquid-transfer layer is immediately adjacent said liquid-permeable covering layer.

20. An absorbent article comprising:
an absorbent body,
a liquid-permeable covering layer arranged over a first surface of the absorbent body, and
a liquid-permeable liquid-transfer layer arranged between the absorbent body and the liquid-permeable covering layer, said liquid-permeable liquid-transfer layer being immediately adjacent said first surface of the absorbent body,
wherein the liquid-permeable covering layer comprises a nonwoven material with a pore volume distribution curve with a maximum at a pore radius greater than or equal to 50 μm and with a wetting angle of at least 120°, and wherein the liquid-permeable covering layer comprises fibers with a fiber fineness of at least 5 dtex, and
wherein the liquid-transfer layer comprises a fibrous layer with a pore volume distribution curve with a maximum at a pore radius of from 105 to 325 μm and wherein the liquid-transfer layer comprises fibers with a fiber fineness of from 6.7 to 11 dtex.

21. The absorbent article according to claim 20, wherein the liquid-transfer layer has a cumulative pore volume in the pore size range of from 110 to 350 μm which is more than 60% of the total pore volume.

* * * * *